United States Patent [19]

Hahs

[11] 4,437,194
[45] Mar. 20, 1984

[54] INTRAOCULAR LENS ASSEMBLY

[75] Inventor: Gregory L. Hahs, Montclair, Calif.

[73] Assignee: Optical Radiation Corp., Azusa, Calif.

[21] Appl. No.: 352,390

[22] Filed: Feb. 25, 1982

[51] Int. Cl.³ .......................... A61F 1/16; A61F 1/24
[52] U.S. Cl. ........................................................ 3/13
[58] Field of Search ........................................ 3/13, 1

[56] References Cited

U.S. PATENT DOCUMENTS

| 3,922,728 | 12/1975 | Krasnov | 3/13 |
| 4,014,049 | 3/1977 | Richards et al. | 3/13 |
| 4,025,965 | 5/1977 | Siegmund | 3/13 |
| 4,127,903 | 12/1978 | Schachar | 3/13 |
| 4,159,546 | 7/1979 | Shearing | 3/13 |
| 4,174,543 | 11/1979 | Kelman | 3/13 |
| 4,215,440 | 8/1980 | Worst | 3/13 |
| 4,242,760 | 1/1981 | Rainin | 3/13 |
| 4,298,994 | 11/1981 | Clayman | 3/13 |
| 4,328,595 | 5/1982 | Sheets | 3/13 |

FOREIGN PATENT DOCUMENTS

| 32835 | 7/1981 | European Pat. Off. | 3/13 |
| 2556665 | 6/1977 | Fed. Rep. of Germany | 3/13 |
| 1103399 | 5/1955 | France | 3/13 |

OTHER PUBLICATIONS

The Lindstrom Centrex Style 20 Posterior Chamber Lens, Advertisement Surgidev Corporation, 1421 State St., Santa Barbara, Calif., 4 pages, Jan. 4, 1981.

Primary Examiner—Ronald L. Frinks
Attorney, Agent, or Firm—Christie, Parker & Hale

[57] ABSTRACT

An intraocular lens assembly for permanent implantation into either an anterior or posterior chamber of an aphakic human eye is provided. The lens assembly includes four haptic positioners connected around the periphery of a lens body to maintain the lens body in its desired position in the eye.

30 Claims, 4 Drawing Figures

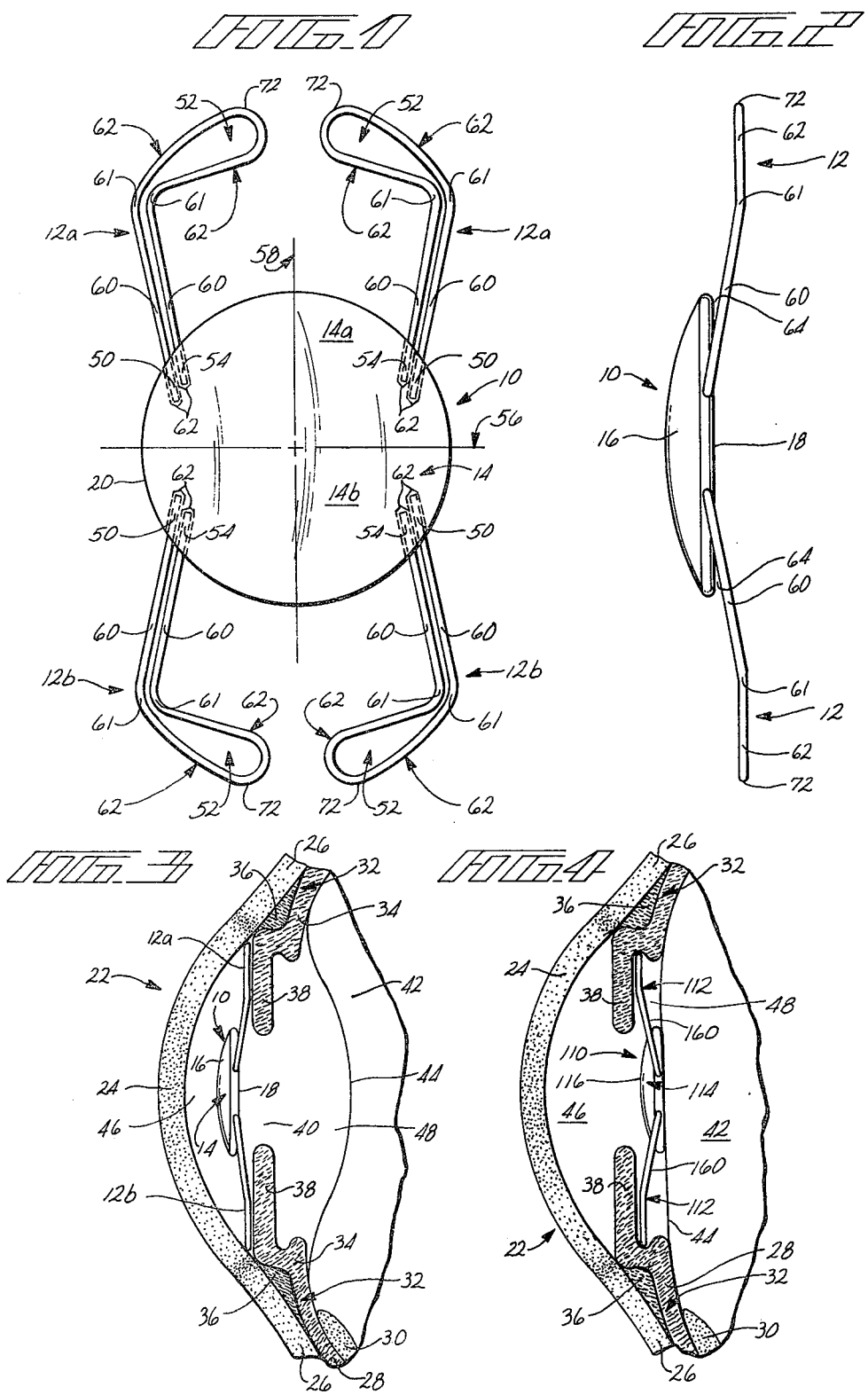

INTRAOCULAR LENS ASSEMBLY

FIELD OF THE INVENTION

This invention relates to an improved intraocular lens assembly for permanent implantation into either the anterior or posterior chamber of an aphakic human eye.

BACKGROUND OF THE INVENTION

The problem of restoring useful vision to a human eye after its cataractus natural lens has been removed has been with us since the introduction of cataract surgery. The solution to this problem has included the use of spectacle lenses, contact lenses, and permanent implantation into the eye of a man-made lens, i.e., an intraocular lens.

Since 1949, when the first implant of an intraocular lens was made, hundreds of thousands of persons have had such implants. Recent advances in cataract surgery have now made the intraocular lens implant procedure a safer and more popular alternative. For example, it is estimated that nearly 40 percent of the people now undergoing cataract surgery select a lens implant, i.e., an intraocular lens, instead of wearing contact lenses or thick cataract-type spectacles.

In addition to advances in surgery which enhance the desirability of intraocular lens implants, there have also been advances in the design of such lenses. Two significant advances in intraocular lens design have been the use of ultrasound eye measurements to determine lens prescriptions and the use of surgical keratometers to reduce visual aberrations (astigmatism) produced by the incision on the cornea. In light of these advances, it is estimated that between about 72 and 82 percent of intraocular lens implant patients achieve 20/40 vision or better.

Although silicate glass was initially considered for use in intraocular lenses, generally such lenses are now made of polymethylmethacrylate. Polymethylmethacrylate is a polymer formed by polymerization of methyl methacrylate monomer.

Both silicate glass and polymethylmethacrylate have many similar properties, e.g., both are inert to body fluids and tissue, are almost perfectly transparent, have constant optical properties, and can be worked mechanically to a high degree of accuracy.

Although polymethylmethacrylate is less hard and, therefore, more easily scratched than glass, it has the major advantage of being lighter in weight (its specific gravity is 1.19 whereas the specific gravity of glass is approximately 3). In addition to the above mentioned properties, polymethylmethacrylate transmits 90 to 92 percent of light, is strong, and can be polished to a smooth finish.

Several methods can be used to form intraocular lenses of polymethylmethacrylate. One such method comprises the steps of coring a lens from a polymethylmethacrylate sheet and machining and polishing the lens to the specifications required for that particular lens prescription. Another method is to injection mold such lenses from polymethylmethacrylate molding material.

As used herein, an "intraocular lens assembly" comprises a lens or lens body as described above formed of glass or polymethylmethacrylate or the like with one or more non-optical "haptic" components or positioners connected to it. Such haptic components are useful for supporting or attaching the lens to the eye and can be formed integrally with the lens or separately and then connected.

In the past, lens assemblies have been provided with haptics having various configurations and properties depending, in part, on the location in the eye into which the lens is to be implanted.

For example, an intraocular lens assembly can be placed in the location of the removed cataractus natural lens, i.e., in the posterior chamber of the eye. This type of lens assembly is referred to herein as a "posterior chamber lens assembly".

A lens implanted in the posterior chamber of the eye is initially maintained in position by the haptic components of the lens assembly contacting the ciliary body or muscle of the eye. However, in time, the vitreous humor in the eye gradually moves toward the implanted lens assembly and eventually adheres to the back side of the lens opposite the iris. Thus, support for maintaining a posterior chamber lens in its proper position is provided by the haptics and, in addition, by the vitreous humor. Because of the support provided by the vitreous humor, the posterior chamber lens haptics do not have to be rigid structural members and, if fact, can be fairly flexible.

One example of an intraocular lens assembly useful for implanting in the posterior chamber of the eye is disclosed in U.S. Pat. No. 4,159,546 to Shearing. The haptics of this lens are a plurality of non-biodegradable strands which are fixed to the lens body and composed of a flexible material. Only one end of each such strand is secured to the lens, with the opposite end being unsecured.

Another type of intraocular lens assembly is designed to be placed into the eye between the iris and cornea, i.e., into the anterior chamber of the eye. This type of lens assembly is referred to herein as an "anterior chamber lens assembly".

Support for a lens positioned in the anterior chamber is provided almost entirely by the haptics connected to the lens. Thus, the haptics provided in the past for an anterior chamber lens have been generally much less flexible than those provided for posterior chamber lenses. Although such stiff haptics can maintain the lens properly positioned within the anterior chamber of the eye, they have been known to cause trauma to the eye when the eye is rubbed or subjected to other forces.

Additionally, when inflexible haptics of such an anterior lens assembly are squeezed together to fit the assembly into an eye having an internal diameter slightly less than that of the assembly, the lens body is caused to move or vault forward or backward. This can result in the lens body being in front or behind its desired position in the eye. Thus, it is presently preferred that each such lens be sized specifically for the eye into which it is to be implanted.

Because of potential injury to the eye when using lens assemblies with inflexible haptics, lenses designed basically for use in the posterior chamber, i.e., lens assemblies with relatively flexible haptics, have been implanted in the anterior chamber. However, the flexible haptics provided by such lens assemblies in the past have provided less than the desired amount of support to the lens body when implanted in the anterior chamber. Thus, their use in the anterior chamber can result in diopter change. If such a lens moves far enough out of position, it can contact the cornea resulting in permanent injury to the eye.

It is, therefore, desired to provide to the art an intraocular lens assembly that, when positioned in either the posterior or anterior chamber of the eye, will readily maintain itself in proper position and additionally will minimize trauma to the surrounding eye tissue. Further, it is desired to provide a lens assembly that can be used for implantation in eyes having a wide range of sizes.

SUMMARY OF THE INVENTION

This invention relates to an intraocular lens assembly for implantation into either the anterior chamber or the posterior chamber of a human eye. The intraocular lens assembly comprises a circular lens body and a pair of haptic positioners for contacting eye tissue to thereby hold the lens body in position in the eye. Each such haptic positioner comprises a monofilament strand connected at both ends to the edge of the lens body for forming a closed loop. The closed loop extends away from the lens body and is narrower at the end adjacent the lens body and wider at the end remote from the lens body. The remote end of one of such loops faces the remote end of the other loop.

DRAWINGS

These and other features, aspects, and advantages of the present invention will be more fully understood when considered with respect to the following detailed description, appended claims, and accompanying drawings, wherein:

FIG. 1 is a plan view of an exemplary embodiment of an intraocular lens assembly provided in accordance with practice of principles of this invention;

FIG. 2 is a side view of the intraocular lens assembly of FIG. 1;

FIG. 3 is a fragmentary schematic view of an exemplary embodiment of an intraocular lens assembly provided in accordance with this invention implanted in the anterior chamber of a human eye; and FIG. 4 is a fragmentary schematic view of another exemplary embodiment of an intraocular lens assembly provided in accordance with this invention implanted in the posterior chamber of a human eye.

DETAILED DESCRIPTION

Referring to FIGS. 1 and 2, there is shown a plan view (FIG. 1) and a side view (FIG. 2) of an exemplary embodiment of an intraocular lens assembly 10 provided in accordance with practice of this invention.

The intraocular lens assembly 10 comprises two pairs of non-optical "haptic" components or positioners 12 connected to a lens or lens body 14. A first pair of such haptic positioners, designated 12a, is on the top half 14a of the lens body and a second pair of haptic positioners, designated 12b, is on the bottom half 14b. When the lens is implanted, the first pair of positioners 12a contacts eye tissue at the top of the eye and the second pair of haptics 12b contacts eye tissue at the bottom of the eye. This eye tissue contact, which is described below in greater detail, enables the lens to be maintained in its desired position within the eye.

In the illustrated embodiment, the lens body 14 is circular and has a "plano-convex" shape, i.e., it has a convex optical surface 16 on one side, a flat or planar optical surface 18 on its other side, and a circular peripheral edge 20. If desired, lenses having other configurations can be provided in accordance with this invention.

The lens body 14 of this embodiment is polymethylmethacrylate, but if desired other biologically inert materials such as glass can be used.

Referring now to FIG. 3, there is shown a schematic view of a human eye 22 with the exemplary intraocular lens assembly 10 implanted therein.

The eye 22 comprises a transparent cornea 24 which connects with the sclera 26, better known as the white of the eye. The sclera extends substantially around the entire eye except for the region of the cornea. In the rear portions of the eye, the choroid 28 overlays the interior surface of the sclera and the retina 30 overlays the interior surface of the choroid. Near the front of the eye, the choroid joins with the ciliary body 32. The ciliary body includes the ciliary process 34 and the ciliary muscle 36. Extending from the ciliary body is the iris 38 which defines the pupil 40.

The interior of the eye is substantially filled with vitreous humor 42 with the hyloid membrane 44 covering the surface of the vitreous humor. The anterior chamber 46 of the eye is between the iris 38 and the cornea 24. The posterior chamber 48 of the eye is located between the iris and the vitreous humor. The natural lens, not shown in the drawings herein, occupies the posterior chamber 48 when it is in place.

In this embodiment, the lens assembly 10 is in place in the anterior chamber 46 with the lens body 14 between the pupil and the cornea. The convex surface 16 of the lens is facing the front of the eye and the planar surface 18 is vertical and facing the rear or back of the eye. The pair of haptics 12a contacts the top inner surface of the eye at about the juncture of the cornea and the iris, while the pair of haptics 12b contacts the bottom inner surface of the eye, also at the juncture of the cornea and iris. As mentioned above, the haptics maintain the lens body in its proper position within the eye.

Although an intraocular lens assembly can be described in terms of any orientation in space, for purposes of exposition herein, the position of the lens assembly components relative to each other are described as if the lens is positioned as described above and shown in FIGS. 1, 2, and 3. Thus, the planar surface 18 of the lens is vertical, the top half 14a of the lens extends toward the top of the eye, the bottom half 14b of the lens extends toward the bottom of the eye, and the convex surface 16 of the lens faces the anterior or front surface of the eye.

The haptic positioners 12 provided in accordance with this invention are preferably formed of a thin strand or filament of material that is biologically inert, i.e., that does not react with eye tissue or fluids. The material must also be resilient and have a "memory" so that such a haptic will bend when forces are applied, yet will tend to spring back into its original shape when the forces are removed.

Preferably, each such haptic 12 is a monofilament strand of a polymeric material such as polypropylene or polymethylmethacrylate or the like. Because the lens of the illustrated embodiment is polymethylmethacrylate, it is most preferred that the haptics also be polymethylmethacrylate. Having the entire lens assembly 10 formed of polymethylmethacrylate enhances the compatibility of the assembly with the eye.

Referring again to the embodiment of FIGS. 1 and 2, each haptic 12 is a polymethylmethacrylate monofilament strand connected at its first end 50 to the peripheral edge 20 of the lens body. The filament extends away from the lens body 14 at the connection of the first end 50, forming a bight 52 remote from the lens body. The filament extends back from the bight 52 towards the lens body and the second end 54 of the filament is also connected to the edge 20. Thus, each haptic 12 comprises a filament connected at both of its ends to the edge of the lens body, to thereby form a closed loop which extends away from the lens.

Polymethylmethacrylate filaments are formed into a haptic having a desired size and shape by first cutting the filament to its desired length. The cut filament is then placed in a groove cut into a metal profile in the shape of the haptic. After the filament is in the metal groove, it is heated to a desired temperature for a selected period of time. When the heating step is completed, the filament is allowed to cool so that it permanently sets in its desired shape. The haptic is then removed from the profile and, after its dimensions are checked, it is ready for attachment to the lens body.

In one embodiment of forming such haptics, the filaments are heated for about 10 minutes at about 165° F. and are then allowed to cool for about 30 minutes before being removed from the profile. It has been found that temperatures much above 165° F. can cause polymethylmethacrylate filaments to soften to an undesirable extent, whereas temperatures much below 165° F. do not result in a desirable permanent set of the haptic.

Referring again to FIGS. 1 and 2, the haptics 12 are preferably positioned around the periphery of the lens body 14 so that the lens assembly 10 is symmetrical about a horizontal axis 56 passing across the width of the lens through its center. Additionally, the lens assembly is preferably symmetrical about a vertical axis 58 which also passes across the width of the lens and through its center.

It is preferred that haptics are positioned as described above so that forces exerted by eye tissue when the lens is in place are transmitted generally uniformly to the lens. This enhances the maintenance of the lens within the eye in its desired horizontal and vertical positions, with the planar surface 18 of the lens maintained in a vertical plane.

Preferably, the size and shape of each haptic 12 is the same. In the illustrated embodiment, each such haptic comprises a pair of opposed filament segments or legs 60 adjacent the lens body edge 20, a pair of filament segments 61 comprising a bend, and a pair of filament segments 62 comprising the bight 52.

The filament segments 60 are preferably parallel to each other as they extend away from the lens body. The filament segments 62 diverge from each other to thereby form the bight 52 and the segments 61 connect the parallel legs and bight. Thus, each such haptic is narrower at its end adjacent the lens body and wider at its end remote from the lens body. Both opposed filament segments 62 of each haptic are preferably in a plane parallel to the plane of the lens, i.e., parallel to the planar surface 18 of the lens. Additionally, it is preferred that the bights 52 are all in the same plane and that the bights or remote ends of the loops of each pair of haptic positioners 12a and 12b generally face each other. This is best seen in FIGS. 1 and 2.

It is preferred that the haptics not extend a great distance past the periphery of the lens body in a horizontal direction, i.e., past the side of the lens body. When the haptics extend beyond the side of the lens, the size of the incision in the eye may have to be increased in order to pass the lens assembly through it for implantation.

When the loops of each pair of haptics face each other, i.e., face inwardly toward the vertical axis 58, the connection points of the haptics can be fairly close to the horizontal axis 56 without any or only a small portion of the haptics extending past the side of the lens. This wide spacing of the haptic connections enhances the stability of the lens when it is in the eye.

Additionally, because each haptic comprises two filament segments or legs 60, the lens resists being twisted about its vertical axis 58 much more than if each haptic had only one such leg or segment. This resistance to torsion or twisting about the vertical axis enhances maintenance of the lens in its proper position within the eye. Even though the haptics provided in accordance with this invention inhibit the lens from being twisted about the vertical axis, they flex readily inwardly toward the center of the lens for enhancing the ease of implantation of the lens into the eye.

To connect each of the four haptics 12 to the lens body 14, four pairs of holes 62 are drilled into the edge 20 of the lens body. The holes of each pair 62 are spaced from each other so that the free ends of each of such preformed haptic loop 12 will register therein. Further, as described above, it is preferred that each pair of holes is as close to the axis 56 without allowing the haptics 12 to extend beyond the side of the lens when they are in place. When the ends 50 and 54 of each such preformed haptic are in place in a pair of holes 60, they are permanently connected to the lens by heat staking or the like.

The axes of the holes are aligned so that the parallel filament segments or legs 60 define a desired angle with the planar surface 18 of the lens. Preferably, the angle defined between the axis of each such hole 62 and the planar surface is the same so that each haptic 12 will extend at the same angle from the lens body. The desired magnitude of this angle can depend, inter alia, upon whether the lens is to be inserted into an anterior or posterior chamber of the eye and upon the desires of the particular surgeon who will use the lens.

In the illustrated embodiment of FIGS. 1 and 2, the parallel filament segments 60 define an acute angle 64 with respect to the plane of the lens body and extend away from the convex surface 16. If desired, however, the segments 60 can extend in a plane parallel to the planar surface or can form an acute angle with the planar surface and extend toward the convex surface 16.

Referring to FIG. 4, for example, there is shown a schematic view of an eye 22 with another embodiment of an intraocular lens assembly 110 provided in accordance with this invention implanted in the posterior chamber 48. The assembly 110 is similar to the assembly 10 except that the parallel filament segments 160 of the haptics 112 extend towards, rather than away from, the convex surface 116.

In this embodiment, the haptics 112 contact the ciliary body 32 to provide support for the lens body 114. It can be seen, however, that the vitreous humor 42 of the eye is in contact with the back or planar surface 118 of the lens body, thereby enhancing the support provided by the haptics.

Referring again particularly to the embodiment of the lens assembly shown in FIGS. 1-3, the legs 60 of each of the haptics extend away from the lens body and define an angle of about 10° with the planar surface 18. Both such legs extend away at a 10° angle at least about half the distance of the overall length of the haptic positioner. The filaments are bent toward vertical at the bend 61 so that the bight portion 52 of each haptic 12 is in a plane about parallel to the planar surface 18. Having the bight portion 52 of each of the haptics in a plane parallel to te plane of the lens tends to minimize forces acting normal to the lens which would tend to dislocate the lens from its proper position in the eye.

The desired size or overall diameter of the lens assembly 10 and shape of the haptic positioners 12, in part, is a function of adult eye size distribution. As used herein, the "overall diameter" is the maximum diameter of the assembly measured from the distil tips of the haptics.

Most eyes have been found to have an internal diameter of from about 11.5 mm to about 13.5 mm in both the anterior and posterior chambers. Preferably, therefore, the overall diameter of the lens assembly is about 13.5 mm when the haptics are in their fully extended position as shown in FIGS. 1 and 2 and about 11.5 mm when the haptics are in their fully compressed position. This minimizes the inventory of different size lens assemblies required. Thus, one size lens assembly can be implanted in most eyes. If desired, however, lens assemblies having other dimensions can be provided in accordance with this invention.

As stated above, the haptics 12 are shown in FIGS. 1 and 2 in their fully extended position. When the eye into which the lens assembly is implanted has an inside diameter of about 13.5 mm, the points 72 on that portion of the bight 52 of each haptic 12 remote from the lens body will be the only haptic points contacting the top and bottom inside surface of the eye. If, however, the eye is smaller than 13.5 mm, the haptics will be compressed when implanted and will tend to flex toward the lens body around the bend or joint 61. The bights will be bent in their vertical plane toward each other and towards the lens body until the opposed filament segments 61 at the bend touch each other. This is considered the fully compressed position of the haptics.

The filament segments 60 or legs 60 will not bend as readily as the segments 61 at the bend because of their configuration.

When the haptics are in their fully compressed position, the overall diameter of the lens assembly is about 11.5 mm. Thus, when the lens assembly 10 is implanted in an eye having a diameter of about 11.5 mm, the entire outer filament of each bight is in contact with eye tissue at the top and bottom of the eye.

A test was conducted on a working model of a lens assembly provided in accordance with this invention, having the above described overall dimensions. This test was to determine the magnitude of vaulting or movement of the lens body 14 in a horizontal direction when the haptics are compressed from their fully extended position to their fully compressed position. When the haptics were compressed, the lens body was found to move horizontally only about 0.13 mm. This amount of vault is insignificant and is many times less than the movement expected when, as in the past, relatively less flexible haptics are used on anterior chamber lens assemblies.

Thus, the above working embodiment provided in accordance with this invention can be implanted satisfactorily in eyes having a diameter as large as 13.5 mm and as small as 11.5 mm.

Although this invention has been described in considerable detail with reference to certain versions thereof, it will be understood that variations and modifications can be effected within the spirit and scope of this invention described above and defined in the following claims.

What is claimed is:

1. An intraocular lens assembly for implantation into the human eye comprising:
   (a) a lens body; and
   (b) a pair of haptic positioners for contacting eye tissue to thereby hold the lens body in position in the eye, each such haptic positioner comprising a filament connected at both ends to the edge of the lens body for forming a closed loop extending away from the lens body, the closed loop being narrower at the end adjacent the lens body and wider at the end remote from the lens body, with the remote end of one of such loops facing the remote end of the other loop.

2. An intraocular lens assembly according to claim 1 wherein the filament comprises polymethylmethacrylate.

3. An intraocular lens assembly according to claim 1 comprising two pairs of haptic positioners, a first pair connected to the edge of the lens body on the top half of said lens body and a second pair connected to the edge of the lens body on the bottom half of said lens body.

4. An intraocular lens assembly according to claim 3 wherein the first and second pairs of haptic positioners are positioned so that the lens assembly is symmetrical about a horizontal axis passing across the width of the lens body and through its center.

5. An intraocular lens assembly according to claim 3 wherein the first and second pairs of haptic positioners are positioned so that the lens assembly is symmetrical about a vertical axis passing across the width of the lens body through its center.

6. An intraocular lens assembly according to claim 1 wherein the remote ends of such loops are in a plane about parallel to the plane of the lens body.

7. An intraocular lens assembly comprising:
   (a) a lens body for implantation in a human eye having front and rear optical surfaces and a peripheral edge; and
   (b) two pairs of haptic positioners for contacting eye tissue to thereby hold the lens body in position in the eye, each such haptic positioner comprising a filament connected at its first end to the peripheral edge of the lens body, the filament extending away from the lens body at the connection of the first end, forming a bight remote from the lens body, and extending back from the bight towards the lens body with the second end of said filament connected to the peripheral edge of the lens body, the bights of each such pair of haptic positioners generally facing each other.

8. An intraocular lens assembly according to claim 7 wherein the filament comprises polymethylmethacrylate.

9. An intraocular lens assembly according to claim 7 having a diameter of about 13.5 millimeters when the haptic positioners are in their fully extended position and a diameter of about 11.5 millimeters when the haptic positioners are in their fully compressed position.

10. An intraocular lens assembly according to claim 7 wherein each such bight is in a plane about parallel to the plane of the lens body.

11. An intraocular lens assembly for implantation into the human eye comprising:
   (a) a circular lens body having front and rear optical surfaces and a peripheral edge; and (b) two pairs of haptic positioners for contacting eye tissue to thereby hold the circular lens body in position within the eye, the first pair of such haptic positioners on the top half of the lens body and the second pair of such haptic positioners on the bottom half of the lens body, wherein the first and second pairs of haptic positioners are positioned so that the lens assembly is symmetrical about a horizontal axis passing across the width of the lens through its center, each such haptic positioner comprising a polymethylmethacrylate monofilament strand connected at both ends to the peripheral edge of the lens body for forming a closed loop extending away from the lens body, the closed loop being narrower at the end adjacent the lens body and wider at the end remote from the lens body, with the remote end of one of such loops of each pair of loops facing the remote end of the other loop of such a pair of loops, the remote ends of such loops all being in a plane about parallel to the plane of the lens body.

12. An intraocular lens assembly according to claim 11 having a diameter of about 13.5 millimeters when the haptic positioners are in their fully extended position and a diameter of about 11.5 millimeters when the haptic positioners are in their fully compessed position.

13. An intraocular lens assembly for implantation into the human eye comprising:
 a lens body having a vertical axis passing across the width of the lens through its center; and
 at least one haptic positioner for holding the lens body in position in the eye, such a haptic positioner comprising:
 two adjacent parallel legs wherein each such leg is attached at one end to the edge of the lens body and wherein both such legs are on one side of the lens body vertical axis and extend away from the edge of the lens body in a direction away from the vertical axis; and
 a loop connected to the legs extending generally toward the vertical axis with a major portion of the loop being on one side of both legs.

14. An intraocular lens assembly according to claim 13 wherein essentially the entire loop is on one side of both legs.

15. An intraocular lens assembly according to claim 13 comprising a plurality of such haptic positioners with each such positioner having about the same configuration.

16. An intraocular lens assembly according to claim 13 comprising at least two haptic positioners with a first such positioner being on one side of the lens body vertical axis and a second such positioner being on the opposite side of the lens body vertical axis.

17. An intraocular lens assembly according to claim 13 comprising at least one pair of haptic positioners with the loops of the pair of positioners generally facing each other.

18. An intraocular lens assembly according to claim 13 wherein each such leg is connected to the lens body in the same quadrant of the lens body.

19. An intraocular lens assembly for implantation into the human eye comprising:
 a lens body having a vertical axis passing across the width of the lens through its center; and
 at least one haptic positioner for holding the lens body in position in the eye, such a haptic positioner comprising:
 a pair of filament segments, each such segment having an end attached to the edge of the lens body wherein both such filament segments are on one side of the lens body vertical axis and form adjacent parallel legs that extend away from the edge of the lens body in a direction away from the vertical axis;
 a filament segment integral with each such parallel leg at the end of the leg remote from the lens body forming a bend; and
 a filament segment integral with each of the filament segments forming such a bend joined at the end remote from the bend to form a loop, wherein a major portion of the loop is on one side of both legs and the loop extends toward the vertical axis.

20. An intraocular lens assembly according to claim 19 wherein essentially the entire loop is on one side of both legs.

21. An intraocular lens assembly according to claim 20 comprising a plurality of such haptic positioners with each such positioner having about the same configuration.

22. An intraocular lens assembly according to claim 19 comprising at least two haptic positioners with a first such positioner being on one side of the lens body vertical axis and a second such positioner being on the opposite side of the lens body vertical axis.

23. An intraocular lens assembly according to claim 19 comprising at least one pair of haptic positioners with the loops of the pair of positioners generally facing each other.

24. An intraocular lens assembly according to claim 19 wherein the pair of filament segments forming the adjacent parallel legs of such a haptic positioner are both connected to the lens body in the same quadrant of the lens body.

25. An intraocular lens assembly according to claim 13 comprising a first and a second pair of such haptic positioners;
 the first such pair of positioners being on the top half of the lens body and comprising a first positioner on one side of the lens body vertical axis and a second positioner on the opposite side of the lens body vertical axis, the loops of the first and second positioners facing each other; and
 the second such pair of haptic positioners being on the bottom half of the lens body and comprising a first positioner on one side of the lens body vertical axis and a second positioner on the opposite side of the lens body vertical axis, the loops of the first and second positioners facing each other.

26. An intraocular lens according to claim 25 wherein the loop of each such haptic positioner is in a plane about parallel to the plane of the lens body.

27. An intraocular lens assembly according to claim 19 comprising a first and a second pair of such haptic positioners;
 the first such pair of positioners being on the top half of the lens body and comprising a first positioner on one side of the lens body vertical axis and a second positioner on the opposite side of the lens body vertical axis, the loops of the first and second positioners facing each other; and
 the second such pair of haptic positioners being on the bottom half of the lens body and comprising a first positioner on one side of the lens body vertical axis and a second positioner on the opposite side of the lens body vertical axis, the loops of the first and second positioners facing each other.

28. An intraocular lens according to claim 27 wherein the loop of each such haptic positioner is in a plane about parallel to the plane of the lens body.

29. An intraocular lens assembly for implantation into the human eye comprising:
a lens body having a vertical axis passing across the width of the lens through its center; and
two pairs of haptic positioners for holding the lens body in position in the eye, a first such pair of positioners on the top half of the lens body and a second such pair of positioners on the bottom half of the lens body, each such positioner comprising:
two adjacent parallel legs wherein each such leg is attached at one end to the edge of the lens body and wherein both such legs are on one side of the lens body vertical axis and extend from the edge of the lens body in a direction generally away from the vertical axis; and
a loop connected to the legs extending generally toward the vertical axis with a major portion of the loop being on one side of both legs between the legs and the vertical axis;
the first pair of positioners comprising a first positioner on one side of the lens body vertical axis and a second positioner on the opposite side of the lens body vertical axis wherein the loops of the first and second positioners generally face each other; and
the second pair of positioners comprising a first positioner on one side of the lens body vertical axis and a second positioner on the opposite side of the lens body vertical axis wherein the loops of the first and second positioners generally face each other.

30. An intraocular lens according to claim 29 wherein the loop of each such haptic positioner is in a plane about parallel to the plane of the lens body.

* * * * *